United States Patent [19]

Titlow et al.

[11] Patent Number: 4,845,989
[45] Date of Patent: Jul. 11, 1989

[54] METHOD AND APPARATUS FOR DETERMINING ELASTIC CONSTANTS IN TUBES

[76] Inventors: Joseph D. Titlow, 1773 Hawthorn Pl., Boulder, Colo. 80302; Wilmut Brost, 10322 Monterey Cir., Northglenn, Colo. 80221; David T. Hahn, 1506 Denison Cir., Longmont, Colo. 80501

[21] Appl. No.: 93,424

[22] Filed: Sep. 4, 1987

[51] Int. Cl.$^4$ .............................................. G01H 5/00
[52] U.S. Cl. .................................... 73/597; 73/861.38
[58] Field of Search ...................... 73/597, 579, 861.38

[56] References Cited

U.S. PATENT DOCUMENTS

| | | | |
|---|---|---|---|
| 3,720,098 | 3/1973 | Dixon | 73/597 |
| 4,073,007 | 2/1978 | Boivin | 364/508 |
| 4,334,431 | 7/1982 | Kohno et al. | 73/597 |
| 4,353,256 | 10/1982 | Moorey | 73/597 |
| 4,574,615 | 3/1986 | Bower et al. | 73/597 |
| 4,674,332 | 6/1987 | Pace et al. | 73/597 |
| 4,738,143 | 4/1988 | Cage et al. | 73/861.38 |

OTHER PUBLICATIONS

PCB Piezotronics Inc., 3425 Walden Ave., Depew, New York, 14043-2495, *Quartz Sensors,* Catalog 884 (1984), pp. 60, 61, 68 and 112.
Leadbetter, H. M., Weston, W. F., and Naimon, E. R., "Low Temperature Elastic Properties of Four Austenitic Stainless Steels," Journal of Applied Physics, vol. 46, No. 9 (Sep. 1975), pp. 3855–3859.
Ledbetter, H. M., Frederick, N. V., and Austin, M. W., "Elastic-Constant Variability in Stainless-Steel 304," Journal of Applied Physics, vol. 51, No. 1 (Jan. 1980), pp. 305–309.
Ledbetter, H. M., "Sound Velocities and Elastic Constants of Steels 304, 310, and 316," Metal Science (Dec. 1980), pp. 595–596.
Housner, G. W. and Vreeland, Jr., T. *The Analysis of Stress and Deformation,* Published by the Authors (3rd printing 1975), pp. 335–341.
Szilard, J.; *Ultrasonic Testing;* 1982, pp. 588–589, 610–612.

*Primary Examiner*—Stewart J. Levy
*Assistant Examiner*—Robert R. Bell

[57] ABSTRACT

Method and apparatus for determining Young's Modulus of a specimen by measuring the speed at which stress waves, either P-waves or S-waves, propagate therein. An embodiment of the apparatus includes two fixtures which are removably affixed to opposite ends of the specimen. A hammer having an accelerometer affixed to its head is used to strike the first fixture to produce stress waves in the specimen. A timer starts counting in response to an output generated by the accelerometer when the hammer strikes the first fixture. A second accelerometer affixed to the second fixture detects the stress waves and generates an output which causes the timer to stop counting. Further circuitry extracts the measured time, calculates a dispersion time delay based on material and length, and subtracts the dispersion time delay and a predetermined constant, both dependent on the material in the specimen, from the measured time to form a corrected transit time. The circuitry uses the corrected transit time to determine the propagation speed of the stress waves and Young's Modulus therefrom.

13 Claims, 5 Drawing Sheets

METHOD AND APPARATUS FOR DETERMINING ELASTIC CONSTANTS IN TUBES

BACKGROUND OF THE INVENTION

1. Field of the Invention

The invention relates to method and apparatus for determining elastic constants in metals, and in particular in metal tubes.

2. Description of the Prior Art

Coriolis mass flow rate meters are used to measure the mass flow of a process fluid. As disclosed in the art, such as in U.S. Pat. No. 4,491,025, issued to J. E. Smith et al. on Jan. 1, 1985, one typical type of Coriolis mass flow rate meter contains two parallel flow conduits, each typically being a U-shaped metal tube. Each metal tube is driven to oscillate about an axis to create a rotational frame of reference. For such a U-shaped metal tube, this axis can be termed the bending axis. As process fluid flows through each oscillating metal tube, movement of the fluid produces reactionary Coriolis forces that are perpendicularly oriented to both the velocity of the fluid and the angular velocity of tube. These reactionary Coriolis forces cause each tube to twist about a torsional axis, that for a U-shaped metal tube, is normal to its bending axis. The amount of twist is proportional to the mass flow rate of the process fluid that flows through the tube.

In practice, the above-described Coriolis mass flow rate meters often required a zero-level offset adjustment. This offset adjustment properly calibrates the meter by reducing the measured mass flow rate to zero when no fluid flows through the meter. Further, it has been found that in manufacturing these meters the zero-level offset adjustment value can be large in many cases and, in addition, fluctuate between various values when the meter is in use. The source of this large zero-level offset adjustment value and its fluctuation has not been recognized in the prior art.

In light of this, a need exists to determine the cause of the large zero-level offset adjustment values and the fluctuation thereof in order to provide more reliable and accurate Coriolis mass flow rate meters than has been heretofore possible.

SUMMARY OF THE INVENTION

We have discovered that the elastic properties of metal tubes used to fabricate flow conduits for Coriolis mass flow rate meters are important in determining the natural frequency, sensitivity and zero-level offset of these meters. In particular, we have discovered that the above-described problem of zero-level offset adjustment values and the fluctuation thereof occurs whenever the value of Young's Modulus of one of the metal tubes used in a double tube Coriolis mass flow rate meter varies significantly from that of the other tube. In fact, we have found such variation in Young's Modulus to be as large as approximately 11 percent in practice.

Notwithstanding the above discovery, various static and dynamic methods known in the art for determining Young's Modulus of a tube do not provide a method or apparatus suitable for use in an industrial environment. In particular, the following known methods for measuring or inferring a value of Young's Modulus all have one or more drawbacks. A first "deformation test" requires that a specimen be clamped in a cantilevered manner. A known force is then applied to the free end of the specimen and the deflection thereof is measured. Young's Modulus is calculated using this measured deflection. Unfortunately, the results of this method are generally not reproducible and the results are sensitive to end effects, i.e., the measured value of Young's Modulus changes with variations in clamping force. Thus, the measured value changes if the clamp is tightened or loosened. A second "axial tensile test" requires that a specimen be clamped at both ends. The specimen is pulled and Young's Modulus is calculated using the measured value of the force required to extend the specimen a specified distance. Unfortunately, because the cross-sectional area of the tube is not uniform along its length, the measured value for Young's Modulus can vary at least three percent. In a "cantilever beam free vibration test" the specimen is clamped at one end. The specimen is then displaced by impact at, for example, the free end and the natural frequency of oscillation thereof is measured. Young's Modulus is then calculated using the measured value of the natural frequency. A drawback of the "cantilever beam free vibration test" is that the results are sensitive to end effects, i.e., the measured value of Young's Modulus changes with variations in clamping force. Lastly, a "suspended bar test" requires that a specimen be hung or suspended from, for example, a line and an accelerometer be affixed to one end of the specimen. The suspended specimen is then struck with a hammer at, for example, its other end to excite axial or longitudinal oscillations therein. The natural frequency of this mode of oscillation is measured and Young's Modulus calculated using the measured value of the natural frequency. With a tube as a specimen it is difficult to reliably and repeatedly strike the end of the tube due to its small cross-sectional area. In addition the set-up time to conduct this test can be lengthy.

Embodiments of the present invention advantageously solve the above-identified problems in the prior art methods and apparatus for measuring Young's Modulus by providing a method and apparatus for measuring the speed at which stress waves, either P-waves or S-waves, propagate in specimens. The inventive method and apparatus find particular use in an industrial environment because it is independent of end effects and the surface upon which the specimen is supported during the test. The only exception is that the specimen should not be supported on a surface in which stress waves induced therein by the inventive apparatus travel faster on the surface than the stress waves travel in the specimen. Consequently, embodiments of the inventive method and apparatus can be advantageously used to match the tubes used to fabricate a double tube Coriolis mass flow rate meter by enabling one to select tubes that have appropriately similar values of Young's Modulus. Through use of this technique, accurate Coriolis mass flow rate meters can be consistently produced, thereby providing a high degree of quality control.

An embodiment of the inventive method for measuring Young's Modulus of a metal tube comprises the steps of: determining the length and density of the tube; exciting stress waves at one end of the tube; measuring the transit time for the stress waves to travel to the other end of the tube; subtracting a dispersion time delay factor based on the tube length and tube material and a predetermined calibration factor based on the material from the measured transit time to form a corrected transit time, and determining Young's Modulus from the length, density, and corrected transit time.

An embodiment of the inventive apparatus for measuring Young's Modulus of a metal tube comprises: fixture means disposed adjacent one end of the tube; striking means for striking the fixture to introduce P-waves into the tube; a timing means that begins timing in response to an output from a first detection means and stops timing in response to an output from a second detection means; first detection means, disposed adjacent the striking means, for detecting when the striking means strikes the fixture and for sending an output to the timing means; second detection means, disposed at the other end of the tube, for detecting the arrival of P-waves and for sending an output to the timer thereupon; and display means, reponsive to the count of the timer, for displaying the count when the timing means stops counting.

The apparatus and method appropriately modified, for example with an amplitude detecting means, can also be used in the measurement of S-wave travel times that are used for calculation of Young's Modulus and Poisson's ratio.

BRIEF DESCRIPTION OF THE DRAWING

The principles of the present invention may be clearly understood by considering the following detailed description in conjunction with the accompanying drawing, in which.

To facilitate understanding, identical reference numerals have been used to denote identical elements common to the figures.

DETAILED DESCRIPTION

Figure 1:
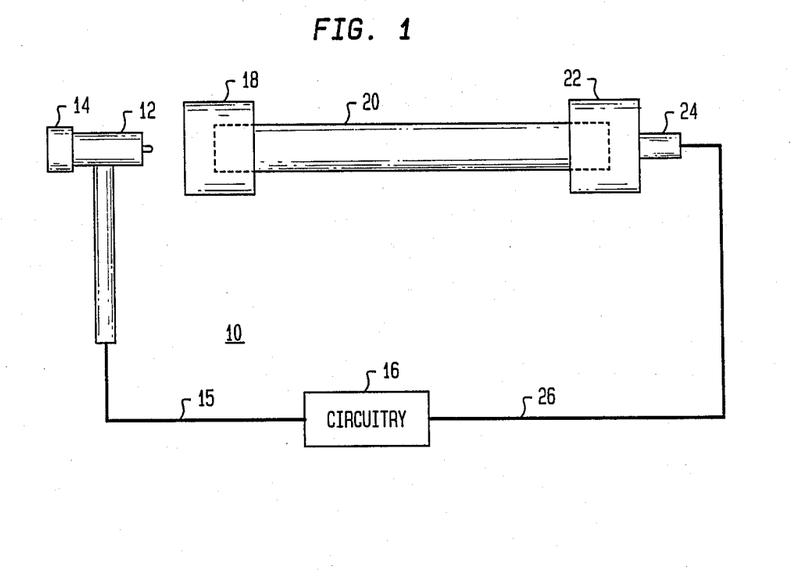
FIG. 1 shows, in pictorial form, an embodiment of the present invention.

FIG. 1 shows, in pictorial form, a preferred embodiment of an apparatus used in determining Young's Modulus of a tube in accordance with the present invention. The tube can be of various lengths and diameter. If discontinuities, such as kinks, nicks, or deep scratches, are present in the tube, it is believed that these discontinuities lead to longer transit times for the stress waves which will lower the value of Young's Modulus. In apparatus 10, instrumented hammer 12 has accelerometer 14 affixed to the head of the hammer. Accelerometer 14 is connected via lead 15 to circuitry 16 whose function will be described in detail below. Striking cap 18 is affixed to one end of tube 20. Cap 22 is affixed to the other end. Accelerometer 24 is affixed to cap 22 and is connected to circuitry 16 via lead 26.

Figure 2:
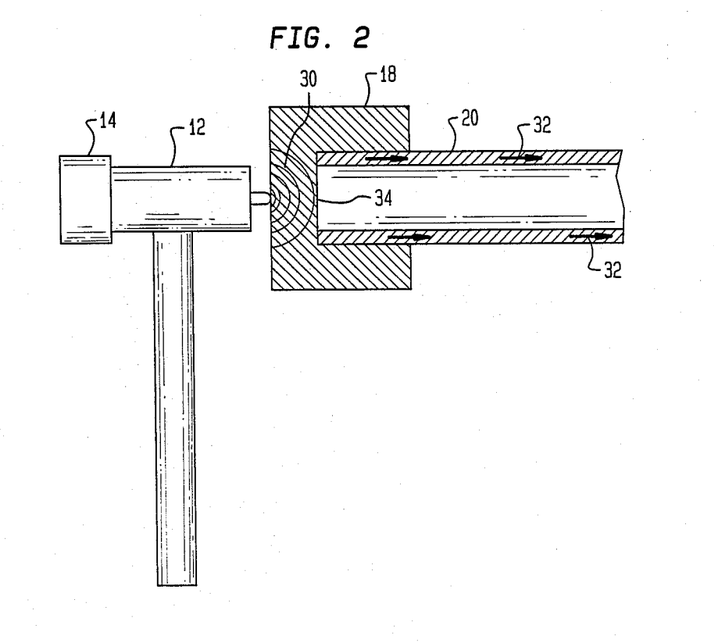
FIG. 2 shows, in pictorial form, the generation of P-waves and the injection thereof into a tube whose Young's Modulus is to be determined.

When the head of hammer 12 strikes cap 18, stress waves 30, as shown in FIG. 2 including both P-waves and S-waves, are generated therein and accelerometer 14 generates an electrical pulse which is detected by circuitry 16 which then begins a timing function. As is known in the art, in general when an axial shock stress is placed on an elastic body, longitudinal waves (also known as compressional or dilatational waves) and shear waves are generated, both of which types of waves propagate in the body. Typically, the longitudinal waves are referred to as P-waves and the shear waves are referred to as S-waves. The velocity of propagation of P-waves in the elastic body is faster than that of S-waves. For tubes, however, the amplitudes of the S-waves are greater than those of the P-waves. Although embodiments of the present invention detect either P-waves or S-waves, to assure maximum accuracy of the resulting measurements, the measurement of P-waves is preferred. The increased accuracy results because the detected wave front is relatively sharp since it only contains energy from one type of wave, namely, P-waves. In contrast, if one were to detect S-waves, the detected wave front would not be as sharp because, in general, it would contain some residual energy from the P-waves along with energy from the S-waves. This would therefore limit the repeatability of the resulting measurements.

Furthermore, as shown in FIG. 2, the propagation of stress waves, i.e. both P- and S-waves, through the cap 18 into the tube 20 is complex. However, cap 18 helps to ensure that the stress waves, including P-waves 30 enter tube 20 in a relatively uniform manner and propagate therein along the direction shown by arrows 32. Cap 18 serves the purposes of (1) helping to provide a uniform wave front at one end of tube 20 and (2) making it easier for an operator to strike the end of tube 20, i.e., without cap 18, an operator would have to strike the narrow edge of the tube. Further, any delay in transit time of P-waves 30 which results form the use of cap 18 and cap 22 is repeatable and can be measured in a calibration procedure and subtracted out from the total transit time measurement made by the inventive P-wave tester.

As shown in FIG. 2, when the wave front representing P-waves 30 reaches end 34 of tube 20, this wave front causes P-waves to be generated in and then propagate down tube 20 toward cap 22. As shown in both FIGS. 1 and 2, accelerometer 24 detects P-waves 30 and, in response, applies an electrical pulse on lead 26 (See FIG. 1) which is connected to circuitry 16 which then stops its timing function. The electrical pulse generated by accelerometer 24 is delayed in time from the electrical pulse generated by accelerometer 14 by an amount which represents the transit time for P-waves 30 to propagate through cap 18, tube 20 and cap 22. Circuitry 16 utilizes this time delay, after correction for the delays caused by caps 18 and 22 and accelerometer 24 to determine a corrected transit time for P-waves 30 to propagate from one end of tube 20 to the other.

Now, once the transit time is known, Young's Modulus, E, is then determined in accordance with the following equation:

$$E = [(1+\nu)(1-2\nu)/(1-\nu)]\rho(L/T)^2 \quad (1)$$

where: $\nu$ is Poisson's ratio, L is the length of tube 20, $\rho$ is the density of tube 20 and T is the transit time of wave front of the P-waves from one end of tube 20 to the other. In accordance with the present invention, $\nu$, L and $\rho$ are determined as follows: (1) Poisson's ratio $\nu$ is essentially constant for the type of materials used to form flow conduits of a Coriolis mass flow rate meter; (2) length L of tube 20 may be measured to suitable accuracy in an industrial environment with a tape measure; and (3) density $\rho$ of tube 20 can be measured to suitable accuracy in an industrial environment in accordance with the following formula for a tube having a circular cross section:

$$\rho = w/(gV) \quad (2)$$

where: w is the weight, g is the gravitational constant and V is the volume of the tube. The volume, V, is calculated by multiplying the area, A, of a cross section of tube 20 by its length L. The area is calculated from the following:

$$A = \pi(d_o^2 - d_i^2)/4 \quad (3)$$

where: $d_o$ is the outer diameter of tube 20 and $d_i$ is the inner diameter of tube 20.

In one embodiment of the present invention circuitry 16 further includes: (1) circuitry through which an operator can supply initial data values such as numerical values of Poisson's ratio and the length and density of tube 20 and a calibration factor for the particular tube material that is used for correcting the transit time, and (2) circuitry that measures the transit time of P-waves propagating in tube 20 and computes Young's Modulus from the initial data and the measured transit time.

Specifically, hammer 12, shown in FIG. 1, is an instrumented hammer that includes accelerometer 14 and is used to excite cap 18 with a nearly constant force over a broad frequency range, the frequency range being determined by the particular hammer structure chosen. Such instrumented hammers having an accelerometer affixed to the head thereof are available from PCB Piezotronics, Inc., 3425 Walden Avenue, Depew, N.Y. 14043. Further, accelerometer 24, which is affixed to cap 22 for detecting P-waves generated in tube 20, may also be obtained from PCB Piezotronics, Inc. Note, as will be described in detail below, cap 22 is in intimate contact with tube 20.

As had been discussed above, in as much as the inventive method and apparatus measures the transit time of P-waves in tube 20 and does not require the tube to be clamped to a base, the orientation of the inventive apparatus is not critical. Furthermore, the transit time of the P-waves in tube 20 can be measured while the tube is being supported on almost any surface. The only exception being that the tube should not be supported on a surface in which stress waves induced therein by the inventive apparatus travel faster on the surface than P-waves travel through the tube. Thus, for example, since stress waves travel faster in aluminum than in steel, placing a steel tube directly on an aluminum table for measurement could result in accelerometer 24 detecting stress waves traveling through the aluminum table before detecting P-waves traveling through the steel tube. Nevertheless, even this problem can be eliminated if the steel tube is supported by foam or rubber pads. The foam or rubber pads act to substantially prevent stress waves from being induced in the aluminum table.

The efficacy of the inventive method and apparatus in an industrial environment is such that we can achieve at least 1 percent accuracy in the measurement of Young's Modulus even when the length of tube 20 is determined with a tape measure. Thus, when tube 20 is 20 feet (approximately 6.1 meters) long, its length need only be determined to within a tolerance of $\pm\frac{1}{4}$ inch (approximately 0.6 centimeters) for a 0.2 percent accuracy in Young's Modulus, whereas, when tube 20 is 2 feet (approximately 61 centimeters) long, its length need only be determined to within a tolerance of $\pm 1/32$ inch (approximately 0.08 centimeters) for a 0.3 percent accuracy in Young's Modulus. This tolerance is determined by expanding Eq. (1) in a Taylor series about the correct length and ascertaining the error induced in Young's Modulus by a particular error in the length of tube 20. Specifically, the fractional measurement error in Young's Modulus is approximately twice the fractional measurement error in length.

Figure 3:
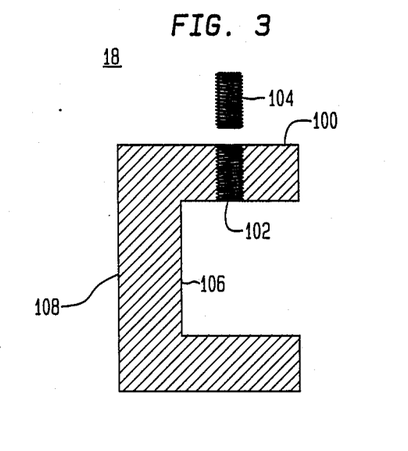
FIG. 3 shows, in pictorial form, striking cap 18 for the embodiment shown in FIG. 1.

FIG. 3 shows, in pictorial form, cap 18 for the embodiment shown in FIG. 1. In FIG. 3, cap 18 comprises cap fitting 100 having a hole 102 drilled in the side thereof. Hole 102 is threaded to permit set screw 104 to be threadably engaged therein. In use, cap fitting 100 is placed over the end of tube 20 so that the end of tube 20 abuts internal face 106. Set screw 104 is then tightened against the side of tube 20 to ensure intimate contact between cap fitting 100 and the end of tube 20. The cap shown in FIG. 3 may also be used to hold accelerometer 24 by drilling and tapping a hole into wall 108 thereof and affixing accelerometer 14 thereto with a threaded stud.

Figure 4:
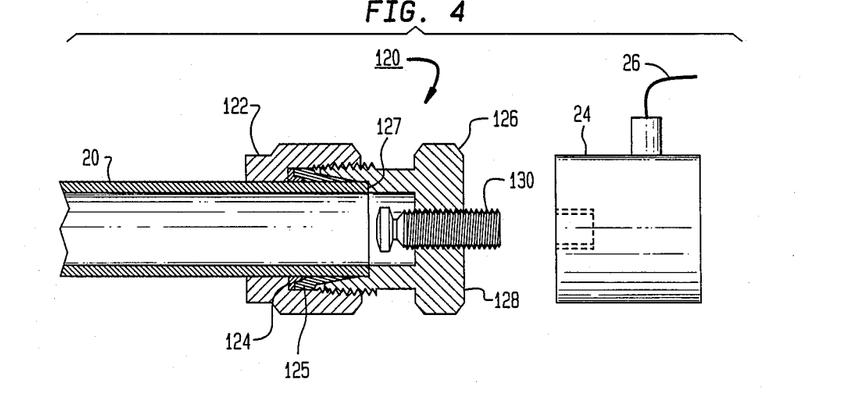
FIG. 4 shows, in pictorial form, an alternative embodiment of cap 22 for affixing accelerometer 24 to tube 20.

FIG. 4 shows, in pictorial form, an alternative embodiment of cap 22 used for affixing accelerometer 24 to tube 20. Fixture 120 is a compressive fitting comprising clamping nut 122, first ferrule or sleeve 124, second ferrule or sleeve 125 and metal seating nut 126. First clamping nut 122 is slipped on tube 20 followed by sleeves 124 and 125 that are disposed within clamping nut 122 on tube 20. Next metal seating nut 126 is slipped onto tube 20 until the end of tube 20 strikes seat 127 provided in metal seating nut 126. Clamping nut 122 has threads on the inside thereof whch are threadably connected with threads on the exterior of metal seating nut 126. When metal seating nut 126 is threaded into clamping nut 122, first sleeve 124 and second sleeve 125 are deformed by forces created by the threading together of clamping nut 122 and metal seating nut 126. This ensures good metal-to-metal contact between tube 20 and seating nut 126. End wall 128 of metal seating nut 126 is drilled and tapped and threaded stud 130 is inserted therein. Accelerometer 24 is threaded onto stud 130. In one embodiment, clamping nut 122, sleeve 124 and metal seating nut 126 are formed from SWAGELOK ® tube fittings in which metal seating nut 126 is modified to threadably accept threaded stud 130 (SWAGELOK is a registered trademark of Crawford Fitting Company of Solon, Ohio). For example for ⅜ inch diameter tubing a SWAGELOK ® fitting having catalog no. 5/8-1010-C is used. For tubing of other diameters, an appropriately sized fitting would be selected. SWAGELOK ® fittings are available from Crawford Fitting Company, 29500 Solon Road, Solon, Ohio 44139. In use, after Young's Modulus is determined in accordance with the present invention, metal seating nut 126 and accelerometer 24 are removed from tube 20 and clamping nut 122 and sleeves 124 and 125 remain affixed thereto. Tube 20 is later cut to remove clamping nut 122 and deformed sleeves 124 and 125. As a result, in this embodiment, clamping nut 122 and defored sleeves 124 and 125 serve as an indication that tube 20 has had its Young's Modulus determined.

Figure 5:
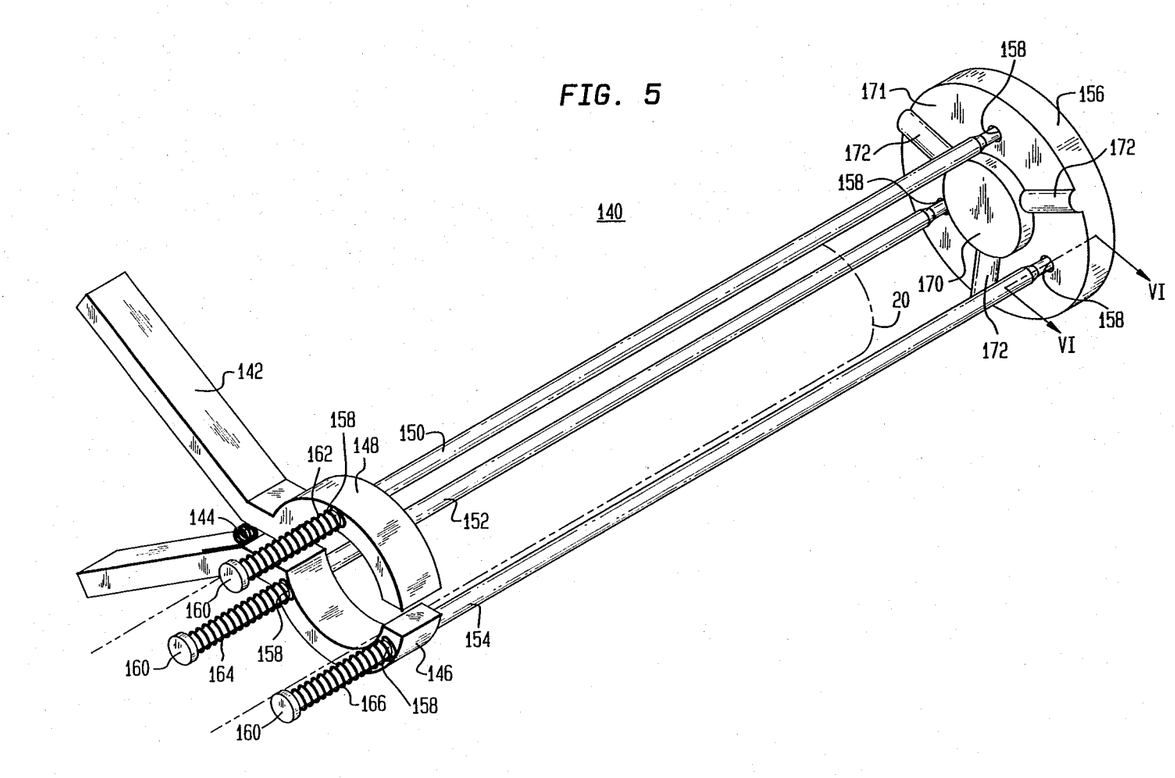
FIG. 5 shows, in pictorial form, a fixture for use in forming striking cap 18 and/or a fixture for accelerometer 24 for the embodiment shown in FIG. 1.

FIG. 5 shows, in pictorial form. fixture 140 for use in forming striking cap 18 for hammer 12, and/or a fixture for accelerometer 24, both shown in FIG. 1. In FIG. 5, fixture 140 comprises clamp 142 loaded with spring 144 and having jaws 146 and 148 shaped to conform to the outer diameter of tube 20. Jaws 146 and 148 each have a layer of rubber or foam (not shown) affixed thereto along their inner surfaces. The rubber or foam layer prevents the jaws 146 and 148 from scratching tube 20 and also damps out stress waves propagating through the fixture 140 into tube 20. Extending from jaws 146 and 148, substantially parallel to tube 20, are three metal tie rods 150, 152 and 154. Tie rods 150, 152, 154 connect clamp 142 to metal plate 156 so that plate 156 is positioned substantially parallel to the end of tube 20. As shown in FIG. 5, plate 156 and jaws 146 and 148 hve correspondingly aligned through holes 158 disposed therein so that tie rods 150, 152, 154 may be inserted therethrough.

In one embodiment, both ends of tie rods 150, 152, 154 are threaded and nuts 160 (see FIGS. 6A–6C) are threaded thereon after tie rods are disposed through holes 158 in plate 156. As shown in FIG. 5, compression 164 and 166 are disposed between the end of tie rods 150, 152 and 154, respectively, and the corresponding through holes 158 in jaws 146 and 148. Compression springs 162, 164 and 166 are held in place by nuts 160 threaded on the end of tie rods 150, 152, 154.

Plate 156 can also be provided with projection 170 on contact surface 171 thereof. Projection 170 may be bullet or cone shaped and is used for guiding an end of tube 20 into intimate contact with pins on contact surface 171 of fixture 140. Preferably, at least three equally spaced, radially extending raised portions, such as metal pins 172, are provided on the contact surface 171. Three pins are shown in FIG. 5. Pins 172 are fixed by conventional fastening means such as glue, welding or brazing. Pins 172 serve as intimate contact points between the end of tube 20 and fixture 150 and allow for any unevenness that can occur at the tube end. Grooves may also be provided in contact surface 171 for receiving pins 172. Alternatively, rounded ridges in contact surface 171 could also be substituted for pins 172.

In operation, jaws 146 and 148 of clamp 142 are opened. Fixture 140 is then slid over and down tube 20 a distance which is sufficient to compress compression springs 162, 164 and 166 to supply a longitudinal force which holds plate 156 and pins 172 in intimate contact with the end of tube 20. If fixture 140 is used to hold accelerometer 24, a hole for a threaded stud may be drilled and tapped in plate 156 as is done for stud 130 for the embodiment shown in FIG. 4.

Figure 6A:
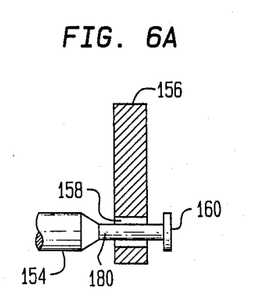
FIGS. 6A, 6B, and 6C, show, in pictorial form, various embodiments of the attachment of the tie rod 154 to plate 156 taken along line VI—VI in FIG. 5.
Figure 6B:
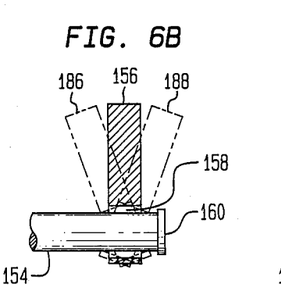
Figure 6C:
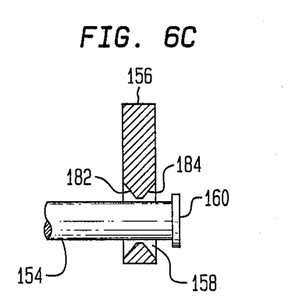

FIGS. 6A, 6B and 6C show in cross-section various embodiments for connection between the plate 156 and the tie rods illustratively tie rod 154, taken along line VI—VI of FIG. 5 for fixture 140 shown in FIG. 5. In FIG. 6A, the diameter of portion 180 of tie rod 154 is reduced in comparison to the diameter of through hole 158 in plate 156. The ends of tie rods 150 and 152 would be similarly fashioned. In FIG. 6B, the diameter of through hole 158 is sufficiently greater than the diameter of tie rod 154, which is not reduced in diameter, to allow a loose fit. As shown by the various dashed lined positions of alignment, 186 and 188, of plate 156 in FIG. 6B, this allows some degree of freedom of motion or wobble between tie rod 154 and plate 156. Also this in turn allows plate 156 to be in intimate contact with the end of tube 20 even though the end of tube 20 is not cut perpendicular to its axial extent. In FIG. 6C, through hole 158 is chamfered. Chamfers 182 and 184 again allow angular movement of plate 156 with respect to tie rod 154. In a further embodiment, the ends of tie rods 150, 152, 154 and plate 156 form ball and socket joints (not shown). Such a ball and socket joint allows relative movement between the tie rods and plate 156 to accommodate misalignment of the end of tube 20 from perpendicularity. An additional advantage of the loose fit in each of these embodiments is that the amount of force required to open the jaws of clamp 142 is reduced. When the clamp 142 is opened, the tie rods, which are typically made of steel and are somewhat stiff, will bend outward away from the tube. The angular rotation of the tie rods reduces the amount of bending that must be done by the tie rods when the clamp 142 is opened whch in turn reduces the amount of opening force required. Note that when fixture 140 is used as a striking cap, intimate contact with the end of tube 20 is assured at the time the fixture is first struck by hammer 12. Once hammer 12 hits plate 156, plate 156 may rebound from the end of tube 20 and even re-strike tube 20. However, by the time such an event has occurred, the initial P-waves have already propagated to the other end of tube 20 and have been detected.

Figure 7:
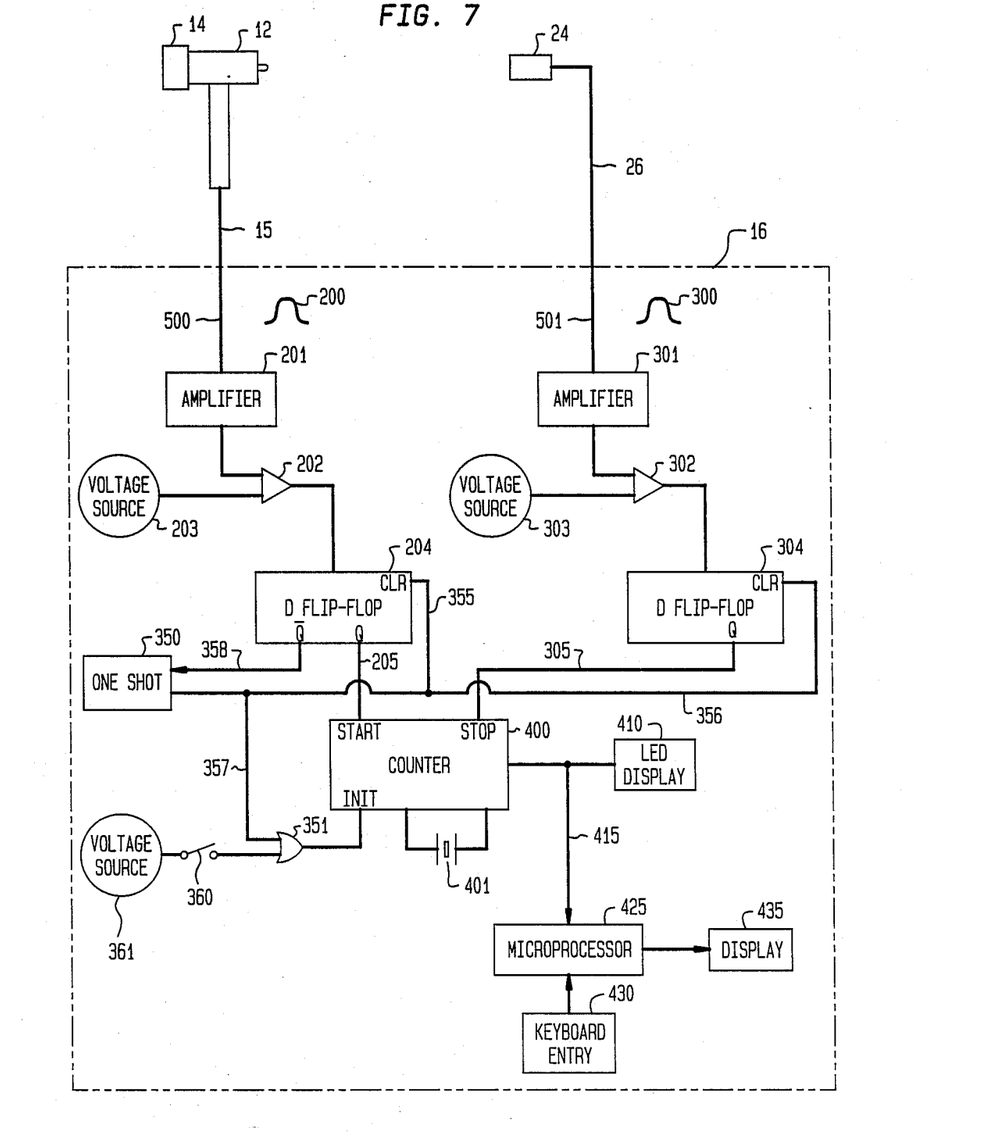
FIG. 7 is a block diagram of circuitry 16 shown in FIG. 1.

FIG. 7 is a block diagram of circuitry 16 shown in FIG. 1. When hammer 12 strikes cap 18 (see FIG. 1), accelerometer 14 affixed to hammer 12 generates electrical pulse 200 on lead 15 as shown in FIG. 7. At the same time, P-waves are generated in tube 20. The P-waves travel toward cap 22 (see FIG. 1) and accelerometer 24. Upon detecting P-waves, accelerometer 24 generates electrical pulse 300 on lead 26 as shown in FIG. 7. Electrical pulses 200 and 300 are applied as input to amplifiers 201 and 301, respectively. In turn, amplifiers 201 and 301 amplify these pulses to a suitable level and apply the resulting amplified pulses as input to amplifiers 202 and 302, respectively. Amplifiers 202 and 302 form noise thresholding circuits. In particular, these amplifiers compare the amplitude of the amplified pulses 200 and 300 generated by accelerometers 14 and 24, respectively, against pre-determined threshold levels set by respective voltage sources 203 and 303. Whenever the amplitude of one of these amplified pulses exceeds the associated threshold level, the corresponding amplifier generates a high level. These threshold levels are set to a sufficiently high level to ensure that circuitry 16 is not triggered by noise.

The output from amplifier 202 is applied as input to D type flip-flop 204 and causes output Q to which lead 205 is connected to go "high." Lead 205 is connected to the START input of counter 400. When output lead 205 goes "high," counter 400 starts counting. Thus, when hammer 12 strikes cap 18 and launches P-waves into tube 20, counter 400 starts counting. The time base and hence the resolution of counter 400 is determined by crystal 401 which typically has a frequency of 10 MHz.

As discussed above, when accelerometer 24 detects P-waves at the end of tube 20, this accelerometer generates pulse 300 which, in turn, produces an output from amplifier 302 which is applied as input to D type flip-flop 304. This causes output Q of this flip-flop which is connected to lead 305 to go "high." Output lead 305 is connected to the STOP input of counter 400. When output lead 305 goes "high," counter 400 stops counting and sends it count to LED display 410. This count represents the transit time of P-waves propagating through caps 18 and 22 and the length of tube 20. After counter 400 outputs its count to LED display 410, the counter is inhibited from further counting for a short period which is sufficiently long to allow any ringing in tube 20 to decay.

Young's Modulus, E, using the corrected transit time is then determined by using Eq. (1). In one embodiment, Eq. (1) can be evaluated by using a programmable calculator and Young's Modulus is determined. In further embodiments of the present invention, Eq. (1) can be evaluated in a processor such as microprocessor. In FIG. 7, microprocessor 425 is provided with the count from counter 400 over lead 415 and with the numerical value of Poisson's ratio $\nu$ and the length L, density $\rho$ of the tube and the calibration factors via an entry device such as keyboard entry device 430. After performing the calculation, microprocessor 425 transmits the result for display to display device 435. The method by which processors such as microprocessor 425 may be interfaced with entry devices such as a keyboard entry device and may be programmed to perform the calculation of Eq. (1) are well known in the art.

In FIG. 7, whenever a pulse is applied as input to flip-flop 204 from amplifier 202 in response to hammer 12 striking tube 20, flip-flop 204 applies at its $\overline{Q}$ output an appropriate level over lead 358 to reset one-shot 350. In response thereto, one-shot 350 generates an output after a delay of, for example, 1.5 seconds. This output is applied over leads 355 and 356 to the clear CLR input of flip-flops 204 and 304, respectively, to reset them and over lead 357 as an input to OR gate 351. The output of OR gate 351 is applied as input to initialization input INIT of counter 400. As a result, circuitry 16 is reset and ready for the next measurement. The delay is chosen to be sufficiently long so that any ringing in the tube will have dissipated. Further, the delay should be sufficiently long that counter 400 is not reset by oneshot 350 before the P-waves generated by hammer 10 are detected by accelerometer 24. This last requirement does not present any practical problem because the P-waves have a transit time which is measured in microseconds whereas the period of one-shot 350 is, for example, 1.5 seconds.

As shown in FIG. 7, counter 400 may also be initialized by manually closing switch 360 which is connected between an appropriate voltage source 361 and an input to OR gate 351.

To determine the accuracy of the present method and apparatus, five certified test bars were obtained from the National Bureau of Standards. The bars were solid and made from aluminum, titanium, stainless steel alloy 321 (SS321), ferrous steel and inconel. The NBS certified mechanical properties of these 5 bars is given in Table 1 rows 1 through 4.

TABLE 1

| Property | Symbol | Units | Al | Ti | SS321 | Ferrous Steel | Inconel |
|---|---|---|---|---|---|---|---|
| Young's Modulus | E | GPa* | 71.39 | 100.5 | 198.7 | 210.1 | 216.7 |
| Poisson's Ratio | $\nu$ | | 0.3413 | 0.3497 | 0.2916 | 0.2851 | 0.2970 |
| Density | $\rho$ | gram · cm$^{-3}$ | 2.711 | 4.822 | 7.865 | 7.829 | 8.241 |
| Longitudinal Velocity | $v_1$ | cm/$\mu$sec | 0.6383 | 0.5780 | 0.5765 | 0.5894 | 0.5925 |
| Length | L | cm | 151.13 | 86.36 | 81.60 | 92.39 | 89.06 |
| NBS Transit Time | $T_o$ | $\mu$sec | 236.8 | 149.4 | 141.5 | 156.8 | 150.3 |

*gigaPascals = $10^9$ newton · m$^{-2}$

Using Eq. (4) below and the values for $v_1$ and L given in Table 1 above, the NBS transit time $T_o$ for each of the test bars can be determined.

$$T_o = L/v_1 \qquad (4)$$

Figure 8:
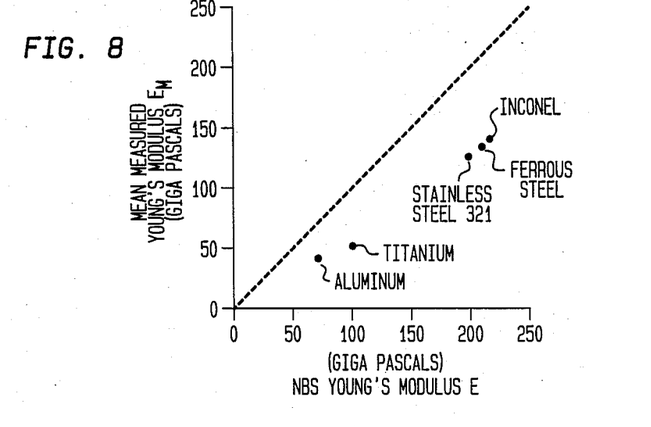
FIG. 8 is a graph showing the relationship between the values of Young's Modulus measured by the National Bureau of Standards and those determined using the apparatus of the present invention for various metal test bars.

The results for $T_o$ are given in row 6 of Table 1. The five test bars were then tested using the circuitry of FIG. 7 and a modified test setup. Accelerometer 24 was mounted directly on the end of the bar using a short mounting stud vice for fixture 120. The instrumental hammer 12 impacted directly on the other end of the bar. Each bar was struck at least 10 times and the transit time, T, was measured via circuitry 16. The measured transit times, T, were consistently higher than the NBS transit time $T_o$. For each test, the measured Young's Modulus, was determined using Eq. (1) and then a mean value, $E_m$, was determined. In FIG. 8 the results of comparing the measured mean value of Young's Modulus, $E_m$, to the NBS value, E, is shown. The dashed line represents the ideal 1:1 relationship between the measured and NBS values for Young's Modulus. For Young's Modulus as determined using the measured transit times, these times T were consistently lower than the NBS values. The difference $\Delta T_1$ between the measured transit time T and the NBS transit time $T_o$ was determined for each test. The values for $\Delta T_1$ for each test bar were averaged to provide a mean $\Delta T_1$. This means $\Delta T_1$ is dependent on the material and can be thought of as a tare value or offset introduced by instrumental hammer 12, accelerometers 14 and 24 and circuitry 16. To determine the effect of fixture 140 and fixture 120 on the measured transit time T, the tests were repeated for each test bar. First, fixture 120 was installed and the tests were run. Both fixtures 120 and 140 were then installed and the tests were rerun. The delay introduced by fixture 120 is designated $\Delta T_2$ and that of fixture 140 is designated $\Delta T_3$. The sum of delays $\Delta T_1$, $\Delta T_2$, and $\Delta T_3$ represents the total tare or offset and is used as a calibration factor $\Delta T$ as shown in Eq. (5).

$$\Delta T_1 + \Delta T_2 + \Delta T_3 = \Delta T = T_T - T_o \qquad (5)$$

where
$T_o$=NBS Transit Time in microseconds
$T_T$=Total Measured Transit Time including delays
Rows 1 through 4 of Table 2 present the delay values measured for each test bar. Again the delay values are mean values in microseconds. Also shown in Rows 5 and 6 of Table 2 are the values for Young's Modulus, designated E (NBS) and $E_M$, respectively, in gigaPascals, as determined by NBS and by the present invention using the calibration factor $\Delta T$ to correct the measured transit time. As can be seen, the differences between the two sets of values for Young's Modulus is extremely small.

TABLE 2

| Description | Units | Al | Ti | SS321 | Ferrous Steel | Inconel |
|---|---|---|---|---|---|---|
| $\Delta T_1$ (mean) | msec | 53.5 | 36.6 | 17.2 | 17.8 | 18.2 |
| $\Delta T_2$ (mean) | msec | 8.9 | 11.6 | 9.9 | 9.4 | 8.8 |
| $\Delta T_3$ (mean) | msec | 10.2 | 10.0 | 9.0 | 12.0 | 9.0 |
| $\Delta T$ (mean) | msec | 72.6 | 58.2 | 36.1 | 39.2 | 36.0 |
| E (NBS) | GPa | 71.39 | 100.5 | 198.7 | 210.1 | 216.7 |
| $E_M$ | GPa | 71.4 | 100.5 | 198.7 | 210.1 | 216.7 |

Calibration factors can be developed for a particular material that is to be tested. However, for industrial purposes it is believed that accurate results will be obtained by selecting a calibration factor $\Delta T$ for a material in the table that most closely matches the material to be tested. The calibration factor $\Delta T$ is subtracted from the measured transit time. The corrected transit time is then used in Eq. (1) to solve for Young's Modulus. This procedure can be performed by the programmable calculator or by providing the microprocessor 425 with the value of the calibration factor. A look-up table could also be used to store various calibration factors that would be selected once the particular material to be tested is known. Other methods of automatically incorporating the calibration factor $\Delta T$ into the determination of Young's Modulus can also be used and those given are for illustrative purposes.

Once the value of Young's modulus for the tube has been determined, the tubes for use in a multiple tube Coriolis mass flow rate meter can be selected. Based on known methods of statistical process control, we believe that a ±4 percent variation in the Young's Modulus of the tubes to be used in a Coriolis meter is an acceptable upper bound and that this will help to alleviate the zero-level offset problem previously described. At first, this variation seems to be greater than that given for the axial tensile test previously described. However, applying the same methods of statistical process control to the ±3 percent variation in the axial tensile test would result in a ±12 percent variation in order to have the same degree of confidence in the axial tensile test as in the test given by the inventive method and device. This ±12 percent variation is in excess of the ±11 percent variation known to cause difficulties.

Figure 9:
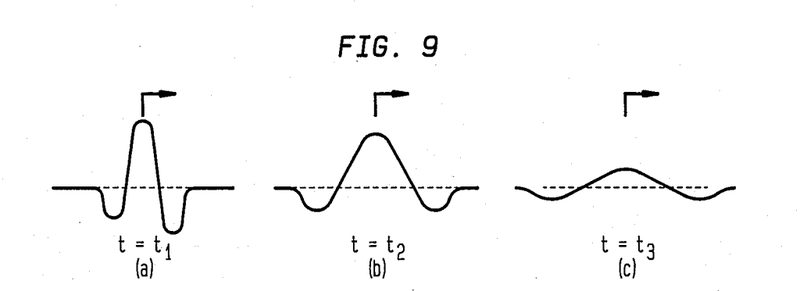
FIG. 9 shows illustrations of the effect of dispersion on stress wave propagation.

An additional correction factor that is dependent on the length L of the tube need also be considered when the tube length is significantly longer than the length of the test bars that are used to develop the calibration factor. Here the NBS test bars were each approximately one meter in length. This correction factor accounts for the dispersion of the stress wave as it travels down the length of the tube. As the stress wave propagates down the tube, it spreads out or disperses. The longer the tube, the more the wave form spreads out. FIG. 9 illustrates the effect of dispersion on a stress wave front as it propagates down the tube at increasing periods of t, $t_2$ and $t_3$ of transit time. The arrow in each of waveforms (a), (b) and (c) in this figure indicates the direction of wave progagation. It can be seen that the wave front becomes less and less steep as transit time increases. Because the circuitry 16 uses a fixed nonzero threshold level to detect the wave front, as the slope of the wave front flattens, it takes longer to reach this threshold, and, hence, an additional time delay is introduced. This dispersive time delay is designated $T_4$. It should be realized that as the length of the tube to be tested approaches the length of the test bar that was used to develop the calibration factor $\Delta T$, dispersion time delay $T_4$ will decrease toward zero. This occurs because the dispersive time delay is inherently included in the calibration factor because it is impossible to have test bar that has a length of zero. Where the tube to be tested is shorter than the test bar used to develop the calibration factor, the dispersive time delay will have a negative value.

The effect of dispersion of the stress wave on Young's Modulus is to decrease the value thereof for longer tubes. This is shown in Tables 3 and 5. The data in Table 3 was collected by measuring the total transit time, $T_T$, using the inventive device, for a 316L stainless steel tube approximately 5.5 meters in length (Tube no. 11). A one meter section was then removed from the tube and the total transit time was again measured for the shortened tube (Tube no. 10). This procedure of cutting and measuring transit times was repeated until 5 tubes each of approximately one meter in length were cut from the original tube. The tube lengths, L, are given at Column 2 of Table 3. The total transit times for these 5 one meter tubes were then measured (Tube no. 1–5). The total transit time (column 3 of Table 3) for each of the tubes was then corrected using the calibration factor $\Delta T$ (column 4 of Table 3) as previously described and Young's Modulus, E, values were determined and are given at Column 5 of Table 3. For the 5 one meter tubes, the mean value for Young's Modulus was 184.8 GPa with a standard deviation of 0.8 percent of the mean. As the length of tube increases, the calculated value of the Young's Modulus drops off for the longest tube to 151.3 GPa, or a drop of 18 percent.

TABLE 3

| Tube No. | L (cm) | $T_T$ ($\mu$sec) | $\Delta T$ ($\mu$sec) | E (GPa) |
|---|---|---|---|---|
| 1 | 93.03 | 202.5 | 36.1 | 184.9 |
| 2 | 93.03 | 203.0 | 36.1 | 183.8 |
| 3 | 93.19 | 202.8 | 36.1 | 184.8 |
| 4 | 92.95 | 203.1 | 36.1 | 183.2 |
| 5 | 93.03 | 201.4 | 36.1 | 187.3 |
| 6 | 121.84 | 260.6 | 36.1 | 174.2 |
| 7 | 218.68 | 456.8 | 36.1 | 159.8 |
| 8 | 311.79 | 642.3 | 36.1 | 156.5 |
| 9 | 404.97 | 829.7 | 36.1 | 154.0 |
| 10 | 498.08 | 1017.1 | 36.1 | 152.5 |
| 11 | 591.19 | 1204.9 | 36.1 | 151.3 |

The data in Table 3 indicate that Young's Modulus is essentially constant for the five one meter tubes. With Poisson's Ratio and the density assumed to be constant for the tube, the speed of propagation, $v_1$, can be calculated by:

$$v_1 = \frac{L}{(T_T - \Delta T)} \quad (6)$$

Table 4 at column 2 shows the speed of propagation, $v_1$, for the 5 one meter tubes (Tube no. 1–5). For these five tubes, the mean $v_1$ is 0.5590 cm/$\mu$sec with a standard deviation of 0.0024 cm/$\mu$sec. This mean value then assumed to be constant for the other tubes (Tube no. 6–11) and was used to find a corrected transit time $T_C$ without dispersion as follows:

$$T_C = L/v_1 \quad (7)$$

This data is shown in Table 4 at column 3. The dispersive time delay $T_4$ is defined:

$$T_4 = (T_T - \Delta T) - T_C \quad (8)$$

Figure 10:
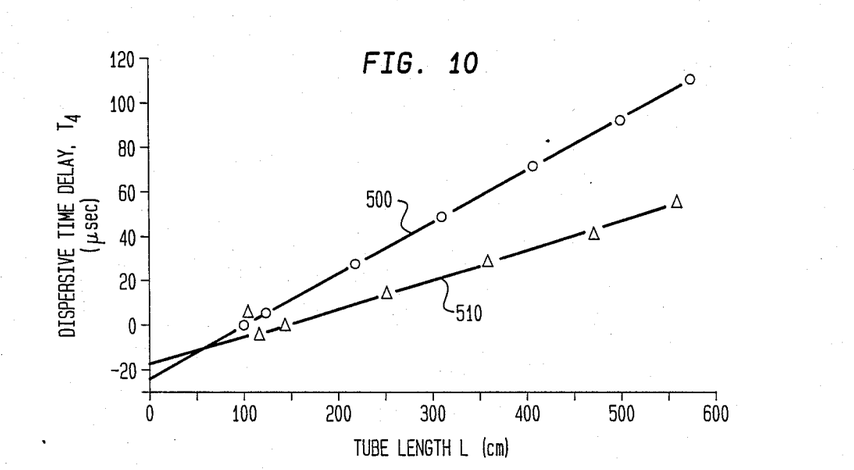
FIG. 10 is a graphical illustration of the relationship between tube length and dispersive time delay.

Column 4 of Table 4 shows that dispersive time delay $T_4$ is approximately zero for the five one meter tubes (Tube no. 1-5) and increases uniformly for the longer tubes. This dependence of the dispersive time delay, $T_4$, on length, L, is shown in FIG. 10 at Curve 500 and is linear over the range tested. A regression analysis on the length and dispersive time delay data yields:

$$T_4 = \alpha_1 L + \alpha_0 \quad (9)$$

with the coefficients $\alpha_1$ and $\alpha_0$ being:
$\alpha_1 = 0.2225$ μsec/cm
$\alpha_0 = -20.6$ μsec The coefficient of determination for this formula is 0.9997. Eq. (9) for a 316L stainless steel tube is graphically represented in FIG. 10 at curve 500.

TABLE 4

| Tube No. | $v_1$ (cm/μsec) | $T_C$ (μsec) | $T_4$ (μsec) | $T_C'$ (μsec) | $E_C$ (GPa) |
|---|---|---|---|---|---|
| 1 | 0.5591 | 166.4 | 0.0 | 166.3 | 185.1 |
| 2 | 0.5574 | 166.4 | 0.5 | 166.8 | 184.0 |
| 3 | 0.5590 | 166.7 | 0.0 | 166.5 | 185.3 |
| 4 | 0.5566 | 166.3 | 0.7 | 166.9 | 183.4 |
| 5 | 0.5628 | 166.4 | -1.1 | 165.2 | 187.6 |
| 6 | 0.5590 | 218.0 | 6.5 | 218.0 | 184.8 |
| 7 | 0.5590 | 391.2 | 29.5 | 392.6 | 183.5 |
| 8 | 0.5590 | 557.8 | 48.4 | 557.4 | 185.1 |
| 9 | 0.5590 | 724.4 | 69.2 | 724.1 | 185.0 |
| 10 | 0.5590 | 891.0 | 90.0 | 890.8 | 184.9 |
| 11 | 0.5590 | 1057.6 | 111.2 | 1057.8 | 184.7 |

Substituting Eq. (9) in Eq. (8) and solving for $T_C$ yields:

$$T_C = T_T - \Delta T - (\alpha_1 L + \alpha_0) \quad (10)$$

Column 5 presents the data, designated $T_C'$ developed when $T_C$ is calculated using Eq. (10) and the values for tube length, $T_T$, and $\Delta T$ for each of the tubes listed in Table 3. As can be seen there is close agreement between the values of $T_C$ and $T_C'$. Column 6 of Table 4 presents the Young's Modulus corrected for all propagation delays including dispersion and is designated $E_C$. As can be seen there is very little variation in the values for $E_C$ even though the tube length goes from approximately 1 meter to about 5.5 meters. For tube lengths in excess of one meter, the previously described procedure for arriving at a corrected transit time can be modified by determining the dispersive time delay $T_4$ using Eq. (9) then subtracting both the dispersive time delay $T_4$ and calibration factor $\Delta T$ from the measured transit time to find the corrected transit time which would then be used in Eq. (1) to solve for Young's Modulus. Again this procedure can be implemented using a programmable calculator or a microprocessor. The coefficients $\alpha_1$ and $\alpha_0$ can be stored in a look up table.

It was thought that coefficients $\alpha_1$ and $\alpha_0$ would not change significantly were another tube material used. Surprisingly, we have discovered that this was not the case. A tube fabricated from HASTELLOY Alloy C-276 alloy (HASTELLOY is a trademark of Cabot Co. of Kokomo, Ind. and HASTELLOY Alloy C-276 alloy is a designation of the Cabot Co.) was tested using a procedure similar to that described for the 316L stainless steel tube. This data is given in Tables 5 and 6.

TABLE 5

| Tube No. | L (cm) | $T_T$ (μsec) | $\Delta T$ (μsec) | E (GPa) |
|---|---|---|---|---|
| 1 | 101.60 | 236.6 | 36.1 | 174.0 |
| 2 | 111.84 | 251.2 | 36.1 | 183.2 |
| 3 | 111.92 | 251.23 | 36.1 | 183.5 |
| 4 | 111.92 | 251.31 | 36.1 | 183.3 |
| 5 | 134.22 | 296.16 | 36.1 | 180.5 |
| 6 | 246.22 | 526.29 | 36.1 | 171.0 |
| 7 | 358.30 | 754.32 | 36.1 | 168.7 |
| 8 | 470.22 | 981.46 | 36.1 | 167.7 |
| 9 | 572.14 | 1193.96 | 36.1 | 165.5 |

TABLE 6

| Tube No. | $v_1$ (cm/μsec) | $T_C$ (μsec) | $T_4$ (μsec) | $T_C'$ (μsec) | $E_C$ (GPa) |
|---|---|---|---|---|---|
| 1 | 0.5201 | 195.3 | 5.2 | 202.0 | 171.7 |
| 2 | 0.5199 | 215.0 | 0.1 | 215.4 | 182.7 |
| 3 | 0.5203 | 215.2 | 0.1 | 215.3 | 183.1 |
| 4 | 0.5201 | 215.2 | 0.0 | 215.4 | 183.0 |
| 5 | 0.5201 | 258.1 | 2.0 | 257.6 | 184.0 |
| 6 | 0.5201 | 473.4 | 16.8 | 474.0 | 182.9 |
| 7 | 0.5201 | 688.9 | 29.3 | 688.4 | 183.6 |
| 8 | 0.5201 | 904.1 | 41.3 | 901.9 | 184.2 |
| 9 | 0.5201 | 1100.1 | 57.8 | 1101.9 | 182.7 |

Again the cut and measure technique used for the 316L stainless steel tube was for the Hastelloy Alloy C-276 tube. Here however four tubes of approximately one meter in length were cut from the original tube. The mean value for $v_1$ was determined using the values for Tubes No. 2-4. This mean value was then used with Tube No. 1 and Tubes No. 5-9 to determine the corrected transit time $T_C$ given at Column 3 of Table 6. The dispersive time delay values were calculated as previously set forth and are shown at Column 4 of Table 6. Column 5 presents the data, designated $T_C'$ developed when $T_C$ is calculated using Eq. (10) and the values for tube length, $T_T$, and $\Delta T$ for each of the tubes listed in Table 5. As can be seen there is close agreement between the values of $T_C$ and $T_C'$. Column 6 of Table 6 presents the Young's Modulus corrected for all propagation delays including dispersion and is designated $E_C$. As can be seen there is very little variation in the values for $E_C$ even though the tube length goes from approximately 1 meter to about 5.5 meters.

Using regression analysis techniques with the length L of Table 5 and the dispersive time delay $T_4$ given in Table 6 the coefficients $\alpha_1$ and $\alpha_0$ in Eq. (9) were found to be:
$\alpha_1 = 0.1221$ μsec/cm
$\alpha_0 = -13.9$ μsec The coefficient of determination for this formula was 0.9973. The values listed for Tube No. 1 were not used to determine the coefficients. Again this relationship is graphically illustrated in FIG. 10 at curve 510. A comparison of the slopes of curve 500 and 510 illustrate the effect of tube material on the dispersive time delay $T_4$.

To account for the dispersive time delay, the previously described procedure for arriving at a corrected transit time is modified. The dispersive time delay $T_4$ is determined using Eq. (9). The dispersive time delay $T_4$ and the calibration factor $\Delta T$ are subtracted from the measured transit time to find the corrected transit time which would then be used in Eq. (1) to solve for Young's Modulus. This is the preferred method. This procedure can be implemented using a programmable calculator or a microprocessor. Again these coefficient values could be stored in a look up table and be selected when the material corresponding to this particular set of coefficients was to be tested. A table of coefficients for other tube materials can be determined using the approach set forth hereinabove.

Although the apparatus and method described are for measuring P-waves, these can also be used to measure S-waves. Because S-waves move along the tube in a direction perpendicular to the longitudinal axis of the tube, accelerometer 24 would be located near the end of the tube on the tube wall, i.e., in a location that would be substantially perpendicular to the longitudinal axis of the tube. The tube is still struck on the opposite end or on the tube wall at the opposite end. If S-wave transit times are measured, then Poisson's ratio $\nu$ can be determined using standard formulas. In addition, measuring S-wave transit times provides a second way to determine Young's Modulus. Circuitry 16 would be modified to suppress detection of the P-waves, which are the first set of stress waves to propagate down the tube, such as by using a time delay and then detecting the S-waves which are the next set of propagating waves. Typically in tubes, S-waves have a significantly greater amplitude than P-waves. Accordingly, a threshold discriminator set for the higher amplitude S-waves can also be used in the modified circuitry to detect and measure the transit time of the S-waves in lieu of or in combination with the previously mentioned threshold discriminator.

Although a particular embodiment of the present invention has been shown and described herein, it should be considered as exemplary only. Many varied embodiments incorporating the teachings of the present invention can be easily constructed by those skilled in the art. For example, the inventive method and apparatus also works when the body whose Young's Modulus is to be determined is not in the shape of a tube. Body as that term is used means a linearly elastic body. Thus, the term body would include all common structual metals such as steel, aluminum or iron. Embodiments of the present invention can be used to determine Young's Modulus of such diverse bodies as beams and tubes which do not have symmetrical cross sections as that of the tube depicted in the drawings. It is intended that the specification be considered as exemplary only with the scope and spirit of the present invention being indicated by the following claims.

We claim:

1. A method for use in manufacturing a Coriolis mass flow rate meter having at least two flow tubes and a reduced zero level offset, said method comprising the steps of:
    testing each one of a plurality of tubular specimens fabricated of substantially the same material in order to determine a value of Young's modulus to a pre-defined accuracy and associated with said one specimen; wherein said testing step comprises the steps of:
        exciting stress waves at a first end of said one specimen;
        measuring a value of transit time for the stress waves to propagate from said first end through said one specimen to a second end thereof;
        measuring values of length and density of said one specimen;
        determining a value of a pre-defined calibration factor and a value of a dispersive time delay factor, wherein said dispersive time delay factor varies in response to the length of said one specimen;
        subtracting both the values of the dispersive time delay factor and the pre-defined calibration factor from the measured transit time value to form a corrected transit time value for said one specimen; and
        generating said associated value of Young's modulus from the length value, the density value and corrected transit time value for said one specimen; and
    selecting specific ones of said tubular specimens for incorporation as corresponding flow tubes within said Coriolis mass flow rate meter wherein all of said specific ones of said tubular specimens possess associated values of Young's modulus that exist within a pre-defined range so as to advantageously reduce zero level offset inherent in said meter.

2. The method in claim 1 wherein the exciting step comprises the step of exciting P-waves at said first end of said one specimen, and said transit time value measuring step comprises the step of measuring the transit time of said P-waves to propagate through said specimen from said first end thereof to said second end thereof.

3. The method in claim 2 wherein the Young's modulus generating step comprises the step of determining said associated value of Young's modulus (E) for said one specimen in accordance with the following equation:

$$E = [(1+\nu)(1-2\nu)/(1-\nu)]\rho(L/T)^2$$

where:
    $\nu$ is Poisson's ratio for the material of which said one specimen is fabricated,
    L is the measured length value of said one specimen,
    $\rho$ is the measured density value of said one specimen, and
    T is the corrected transit time value of said one specimen.

4. The method in claim 3 wherein said pre-defined calibration factor value and dispersive time delay factor value determining step comprises the step of determining a value for the time delay factor ($T_4$) for said one specimen in accordance with the following equation:

$$T_4 = \alpha_1 L + \alpha_0$$

where: $\alpha_1$ and $\alpha_0$ are predetermined coefficients.

5. The method in claim 4 further comprising the step of choosing a tubular specimen fabricated from any material existing within a group of materials consisting of: aluminum, titanium, stainless steel, ferrous steel, inconel and a HASTELLOY alloy.

6. The method in claim 5 wherein said selecting step comprises the step of using, as said pre-defined range, no more than approximately a ±4 percent variation among the value of Young's modulus for said specific ones of said specimens that are to be selected.

7. The method in claim 6 wherein said pre-defined calibration factor value and dispersive time delay factor value determination step further comprises the step of using the value of 0.2225 microseconds/cm for the coefficient $\alpha_1$ and the value of $-20.6$ microseconds for the coefficient $\alpha_0$ if said chosen tubular specimen is fabricated from 316L type stainless steel.

8. The method in claim 6 wherein said pre-defined calibration factor value and dispersive time delay factor value determining step further comprises the step of using the value of 0.1221 microseconds/cm for the coefficient $\alpha_1$ and the value $-13.9$ microseconds for the coefficient $\alpha_0$ if said chosen tubular specimen is fabricated from HASTELLOY type C-276 alloy.

9. A method for use in manufacturing a Coriolis mass flow rate meter having at least two flow tubes and a reduced zero level offset, said method comprising the steps of:

testing each one of a plurality of tubular specimens fabricated of substantially the same material in order to determine a value of Young's modulus to a pre-defined accuracy and associated with said one specimen; wherein said testing step comprises the steps of:

exciting P-waves at a first end of said one specimen;

measuring a value of transit time for the P-waves to propagate from said first end through said one specimen to a second end thereof;

measuring value of length and density of said one specimen;

determining a value of a pre-defined calibration factor and a value of a dispersive time delay factor, wherein said dispersive time delay factor varies in response to the length of said one specimen;

subtracting both the values of the dispersive time delay factor and the pre-defined calibration factor from the measured transit time value to form a corrected transit time value for said one specimen; and generating said associated value of Young's modulus from the length value, the density value and corrected transit time value for said one specimen; and selecting specific ones of said tubular specimens for incorporation as corresponding flow tubes within said Coriolis mass flow rate meter wherein all of said specific ones of said tubular specimens possess associated values of Young's modulus that exist within a pre-defined range so as to advantageously reduce zero level offset inherent in said meter.

10. The method in claim 9 wherein the Young's modulus generating step comprises the step of determining said associated value of Young's modulus (E) for said one specimen in accordance with the following equation:

$$E = [(1+\nu)(1-2\nu)/(1-\nu)]\rho(L/T)^2$$

where:

$\nu$ is Poisson's ratio of the material of which said one specimen is fabricated, L is the measured length value of said one specimen, $\rho$ is the measured density value of said one specimen, and T is the corrected transit time value for said one specimen.

11. The method in claim 10 wherein said pre-defined calibration factor value and dispersive time delay factor value determining step comprises the step of determining a value for the time delay factor ($T_4$) for said one specimen in accordance with the following equation:

$$T_4 = \alpha_1 L + \alpha_0$$

where: $\alpha_1$ and $\alpha_0$ are predetermined coefficients.

12. The method in claim 11 further comprising the step of choosing a tubular specimen fabricated from any material existing within a group of materials consisting of: aluminum, titanium, stainless steel, ferrous steel, inconel and a HASTELLOY alloy.

13. The method in claim 12 wherein said selecting step comprises the step of using, as said pre-defined range, no more than approximately a $\pm 4$ percent variation among the value of Young's modulus for said specific ones of said specimens that are to be selected.

* * * * *